United States Patent [19]

Murray

[11] 4,344,519
[45] Aug. 17, 1982

[54] AUTO-SAMPLER AND FEED CHUTE FOR AN ASPHALT PLANT

[75] Inventor: Donald L. Murray, Appleton, Wis.

[73] Assignee: Allis-Chalmers Corporation, Milwaukee, Wis.

[21] Appl. No.: 167,405

[22] Filed: Jul. 11, 1980

[51] Int. Cl.³ .............................................. B65G 65/32
[52] U.S. Cl. ................................. 193/2 R; 193/31 R
[58] Field of Search ............. 193/2 R, 31 R; 209/910; 414/269

[56] References Cited

U.S. PATENT DOCUMENTS

| | | | |
|---|---|---|---|
| 2,356,096 | 8/1944 | Shallock | 193/31 R X |
| 2,437,302 | 3/1948 | Maxon | 193/31 R |
| 3,842,992 | 10/1974 | Herold | 193/31 R X |

Primary Examiner—Robert B. Reeves
Assistant Examiner—Gene A. Church
Attorney, Agent, or Firm—Robert C. Jones

[57] ABSTRACT

An aggregate feed chute for an asphalt plant includes a diverter wall which may be selectively actuated to capture the entire discharge stream of a material conveyor for sampling purposes without the necessity of moving the feed chute with respect to the drum mixer or the conveyor.

7 Claims, 2 Drawing Figures

AUTO-SAMPLER AND FEED CHUTE FOR AN ASPHALT PLANT

BACKGROUND OF THE INVENTION

Asphalt is a mixture of various size aggregates and asphalt bitumen to make asphaltic concrete. The aggregates are segregated and blended by size in an aggregate blending system and appear as a single flow of material entering the drum mixer. There are State requirements that this blend of aggregate be checked by sampling at various intervals. The most commonly used sampler is a trolley type device which mounts on the head end of the conveyor that is provided to move the blended aggregate to the drum mixer.

The aggregate, composed of a variety of sizes, does not load the conveyor evenly and there is a tendency toward some segregation based upon the size, shape and density properties of each piece. Generally the larger aggregates migrate to the periphery while the smaller sizes are concentrated in the middle of the material stream. Thus, it has been found that the trolley type sampler does not capture a full cross-section of the material discharged from the conveyor due to the discharge characteristics of the material discharging from the moving conveyor. As is known, the discharge characteristics of aggregate from a moving conveyor is in the propensity of the aggregate as it leaves the confines of the conveyor belt to fan radially outwardly. Thus, the larger size aggregate which naturally graviate to the sides of the belt are missed by the known trolley samplers. This coupled with the segregation of the different sizes of the material indicates that a basic sample is not collected.

SUMMARY OF THE INVENTION

Accordingly, this invention provides a material receiving receptacle or feed chute disposed to receive and discharge the aggregate material from a conveyor belt into a drum mix, asphalt plant or storage hopper. The chute includes a provision wherein the entire flow of aggregate from the conveyor belt can be diverted into a distinct separate sampling receptacle for checking of the aggregate blend. The arrangement is automatic and operable at random intervals.

Thus, it is the general object of the present invention to provide an aggregate sampling device capable of capturing the entire discharge stream from the material conveyor.

Another object of the present invention is to provide a feed chute having an automatic operable material sampler.

Still another object of the present invention is to provide an aggregate sampler device which is not a part of the conveyor structure.

DESCRIPTION OF THE INVENTION

Figure 1:
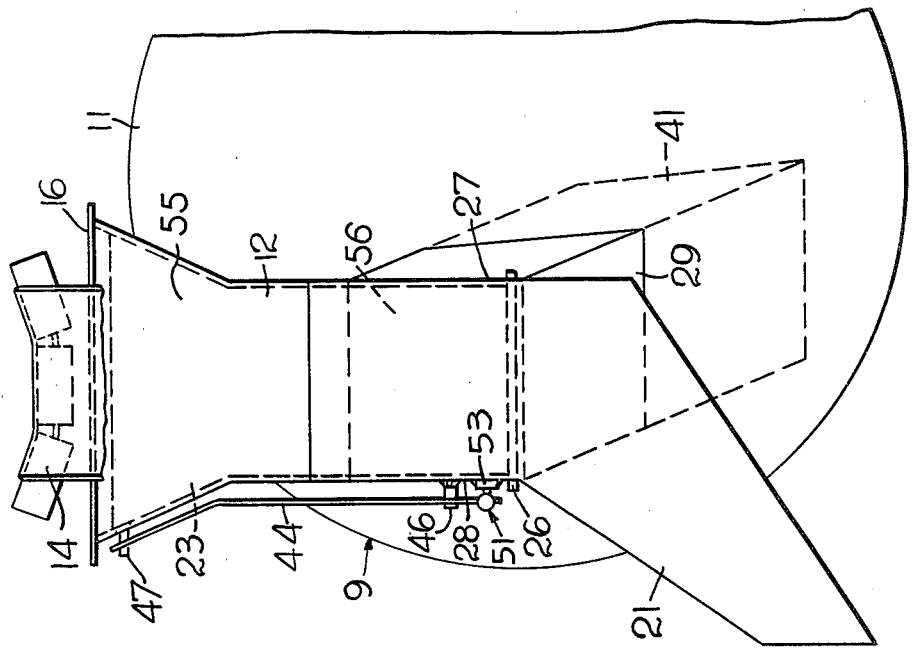
FIG. 1 is a side view of aggregate sampling device and drum mixer.

As shown in FIG. 1, there is illustrated an asphalt mixer 9 which includes a rotary drum mixer 10, the feed end being encased in a stationery shroud 11 and an associated feed chute 12 of the present invention. The feed chute 12 is constructed and arranged to receive the full discharge stream from a material conveyor 14. The aggregate enters the open top 16 of the feed chute 12 and is directed into the drum mixer by a discharge chute 41 having an inlet 56 connected to communicate with the interior of the feed chute.

The feed chute which is constructed of welded plate steel has a bottom wall 55 defining a sampler discharge opening 33. A sampler chute 21 which is connected to the feed chute to enclose the sampler discharge opening 33 is arranged to be in communication with the interior of the feed chute 12. Internally within the feed chute 12 there is provided a material diverter wall 23. As shown, the diverter wall 23 is supported for pivotal movement on a hinge pin or shaft 26. The shaft 26 is supported between a side wall 27 and an opposing side wall 28 of the chute and is located at the junction line where a bottom plate 29 of the discharge chute 41 meets a vertical lower front plate 31 of the sampler chute. The diverter wall 23 is fully as wide as the internal width dimension of the chute 12 and extends upwardly from the shaft 26 to a plane which is short of opening 16. As shown in phantom lines in FIG. 2, the diverter wall 23 is in a position in which it effectively blocks a sampler discharge opening 33 of the sample chute 21. Thus, all the aggregate material deposited into the feed chute 12 by the conveyor 14 will be directed into the discharge chute 41 to enter the drum mixer 10. When it is desired to sample the aggregate, the diverter wall 23 is caused to pivot on the shaft 26 moving to the position indicated by dotted lines in FIG. 2. In this position the diverter wall 23 operates to direct the flow of aggregate from conveyor into the sampler chute 21 which, in turn, discharges into a suitable receptacle (not shown).

Figure 2:
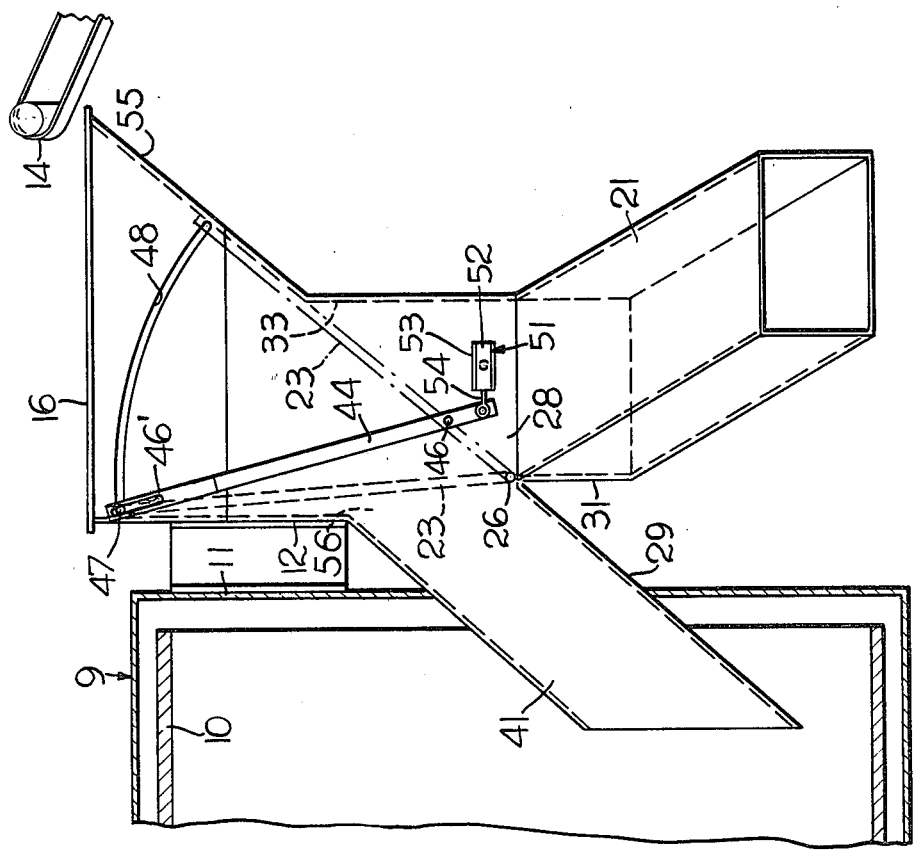
FIG. 2 is a front view of sampling device with the drum shown in section.

Movement of the diverter wall 23 is accomplished by means of a lever 44. The lever 44 is disposed on the external surface of the wall plate 28 and pivots on a pin 46. At its upper end the lever 44 is provided with an elongated slot 46' which receives a pin 47. The pin 47 is secured in and extends outwardly from the edge of the diverter wall 23 and through an arcuate slot 48 formed in the side wall 28 of the feed chute. Thus, pivotal movement of the lever 44 from the full line position, that it occupies as depicted in FIG. 2, in a clockwise direction, will cause the diverter wall 23 to pivot on the shaft 26, in a clockwise direction, as viewed in FIG. 2. This movement, as previously mentioned, will divert the aggregate discharge into the discharge chute 41. When a sufficient representative sample of the aggregate has to be obtained, the lever 44 is caused to pivot in a counterclockwise direction. This will move the diverter wall 23 back to its position wherein the feed chute 41 is blocked.

Automatic operation of the lever 44 is accomplished by operation of a servomotor 51, herein depicted as a pneumatic cylinder 52 and a piston device 54. As shown, the pneumatic cylinder 52 of the servomotor 51 is pivotally supported in a bracket 53 that is welded to the surface of the steel side wall 28. The extending end of the piston 54 is pivotally connected to the lower depending end of the lever 44. Thus, energization of the servomotor 51 to effect the outward or liftward movement of the piston 54, as viewed in FIG. 2, will cause the lever 44 to pivot on pin 46 thereby moving the arm 44 in a clockwise direction to move the diverter wall 23 in the direction to close the sampler chute 21 for receiving the aggregate sample. On the other hand, energization of the servomotor 51 to effect a retraction of the piston rod 54 will effect the movement of the diverter wall 23 to the position depicted in FIG. 2 opening the sampler chute. Energization of the servomotor 51 for selective directional operation can be effected by a remotely located control switch (not shown) which can be conveniently located for ease of access to an operator, or the switch may be connected to a timer mechanism for operation at preselected intervals.

From the foregoing description, it is apparent that a novel feed chute and aggregate sampler for an asphalt plant is provided. The novel arrangement captures the entire discharge stream from the moving conveyor belt. The arrangement eliminates the dependency of support from the conveyor thus eliminating the width restriction imposed by the width of the conveyor.

The embodiments of the invention in which an exclusive property or privilege is claimed are defined as follows:

1. A sampler feed chute assembly for an asphalt plant having a mixing drum and an aggregate conveyor for supplying said mixing drum with aggregate, said assembly comprising:
   a feed chute (12) for receiving the aggregate from the conveyor;
   a discharge chute (41) having an inlet (56) operatively connected to said feed chute to communicate with the interior of said feed chute to direct the aggregate into said drum mixer; and said feed chute having a bottom wall (55) defining a sampler discharge opening (33); ;p1 a sampler chute (21) connected to said feed chute to enclose said sampler discharge opening and establish feed flow communication from the interior of said feed chute to said sampler chute to receive aggregate from said feed chute;
   a selectively operable diverter means (23) within said feed chute operable to be moved to a first stationary position in which said diverter means closes said sampler discharge opening and directs the flow of aggregate to said discharge chute, and operable to be moved to a second stationary position in which said diverter means closes said discharge chute inlet (56) and diverts the aggregate to said sampler chute;
   means for selectively moving said diverter means between said first and second stationary positions; and
   whereby the aggregate flowing from said feed chute into the drum mixer may be selectively diverted to said sampler chute for obtaining a representative sample of the aggregate flowing through said feed chute.

2. A sampler assembly according to claim 1 wherein said feed chute is independently supported free of said conveyor.

3. A sampler assembly according to claims 1 or 2 wherein said feed chute is constructed and arranged to capture the full cross section of the aggregate discharging from said conveyor.

4. A sampler assembly according to claim 3 wherein said diverter means is a diverter wall (23) having one end pivotally mounted within said feed chute and operable when in said first stationary position to close said sampler discharge opening and direct the flow of aggregate to said discharge chute, said diverter wall being operable in said second stationary position to close said discharge chute inlet and divert the discharge of aggregate from the conveyor to said sampler chute.

5. A sampler assembly according to claim 4 wherein said diverter wall (23) is pivotally mounted on a shaft (26); said shaft extending from a side wall (27) of said feed chute to an opposing side wall (28) of said feed chute; said shaft being generally parallel to said bottom wall; said diverter wall having a latitudinal dimension parallel to said shaft sufficient to extend from said side wall (27) to said opposing side wall (28) of said feed chute; and said diverter wall being of a longitudinal dimension extending from said shaft sufficient to close said sampler discharge opening when said diverter wall is moved to said second stationary position and to close said discharge chute inlet when said diverter wall is moved to said first stationary position.

6. A sampler assembly according to claim 5 wherein said means for selectively moving said diverter wall, comprises a lever supported for pivotal movement on an external surface of a side wall of said feed chute;
   said diverter wall having a stud (47) extending outwardly through an arcuate slot (48) formed in said side wall on which said lever is supported; said arcuate slot having a radius of curvature about said shaft (26) equal to the distance between said shaft and said stud; said lever being provided with an opening in which said stud of said diverter wall engages;
   whereby movement of said diverter wall to its first or second position may be accomplished selectively and externally of said feeder chute.

7. A sampler assembly according to claim 6 wherein there is provided a servomotor for operating said lever, said servomotor being supported on the external surface of said wall of said feed chute on which said lever is pivotally supported and in position to be operably connected to said lever.

* * * * *